(12) United States Patent
Malkowski et al.

(10) Patent No.: US 10,973,510 B2
(45) Date of Patent: Apr. 13, 2021

(54) NEEDLE LOADING UNIT FOR SURGICAL SUTURING APPARATUS

(71) Applicant: Covidien LP, Mansfield, MA (US)

(72) Inventors: Jaroslaw Malkowski, Trumbull, CT (US); Jason Pinsonnault, Hamden, CT (US); Tomasz Hejmowski, Derby, CT (US)

(73) Assignee: Covidien LP, Mansfield, MA (US)

( * ) Notice: Subject to any disclaimer, the term of this patent is extended or adjusted under 35 U.S.C. 154(b) by 383 days.

(21) Appl. No.: 15/947,898

(22) Filed: Apr. 9, 2018

(65) Prior Publication Data
US 2018/0317904 A1    Nov. 8, 2018

Related U.S. Application Data

(60) Provisional application No. 62/500,019, filed on May 2, 2017.

(51) Int. Cl.
*A61B 17/04*    (2006.01)
(52) U.S. Cl.
CPC .. *A61B 17/0483* (2013.01); *A61B 2017/0479* (2013.01)
(58) Field of Classification Search
CPC .......... A61B 17/0483; A61B 17/06061; A61B 17/06114; A61B 2017/0479; A61B 2017/06142; A61B 17/04; A61B 17/0469; A61B 17/0491
See application file for complete search history.

(56) References Cited

U.S. PATENT DOCUMENTS

| | | | |
|---|---|---|---|
| 5,478,344 A | * | 12/1995 | Stone ............... A61B 17/0469 206/339 |
| 8,177,794 B2 | | 5/2012 | Cabrera et al. |
| 8,226,667 B2 | | 7/2012 | Viola et al. |
| 8,246,637 B2 | | 8/2012 | Viola et al. |
| 8,292,905 B2 | | 10/2012 | Taylor et al. |
| 8,292,906 B2 | | 10/2012 | Taylor et al. |

(Continued)

FOREIGN PATENT DOCUMENTS

| | | |
|---|---|---|
| EP | 1588666 A2 | 10/2005 |
| WO | 9741780 A1 | 11/1997 |
| WO | 2008045333 A2 | 4/2008 |

OTHER PUBLICATIONS

European Search Report dated Oct. 1, 2018 issued in corresponding EP Appln. No. 18 17 0234.

*Primary Examiner* — Melanie R Tyson
(74) *Attorney, Agent, or Firm* — Carter DeLuca & Farrell LLP

(57) ABSTRACT

A loading unit assembly for use with a surgical suturing apparatus includes a surgical needle and a support structure configured for releasably securing the surgical needle. The support structure may include a first finger and a second finger adjacent to the first finger. The first and second fingers may define a first channel therebetween. The support structure may also include a third finger defining a seat portion and a back portion. The seat and back portions may be in facing relation with the first and second fingers. The third finger and the first and second fingers may define a second channel therebetween. The surgical needle may be loaded in the second channel and may be in abutment with at least the seat portion.

17 Claims, 12 Drawing Sheets

(56) References Cited

U.S. PATENT DOCUMENTS

| | | |
|---|---|---|
| 8,337,515 B2 | 12/2012 | Viola et al. |
| 8,372,090 B2 | 2/2013 | Wingardner et al. |
| 8,454,631 B2 | 6/2013 | Viola et al. |
| 8,460,275 B2 | 6/2013 | Taylor et al. |
| 8,490,713 B2 | 7/2013 | Furnish et al. |
| 8,496,674 B2 | 7/2013 | Cabrera et al. |
| 8,506,581 B2 | 8/2013 | Wingardner, III et al. |
| 8,628,545 B2 | 1/2014 | Cabrera et al. |
| 8,636,752 B2 | 1/2014 | Cabrera et al. |
| 8,747,424 B2 | 6/2014 | Taylor et al. |
| D708,746 S | 7/2014 | Cabrera et al. |
| 8,864,776 B2 | 10/2014 | Bogart et al. |
| 8,968,340 B2 | 3/2015 | Chowaniec et al. |
| 8,968,342 B2 | 3/2015 | Wingardner, III et al. |
| 9,113,860 B2 | 8/2015 | Viola et al. |
| 9,271,723 B2 | 3/2016 | Taylor et al. |
| 9,615,824 B2 | 4/2017 | Furnish et al. |
| 2005/0240199 A1* | 10/2005 | Martinek ........... A61B 17/0483 606/104 |
| 2010/0228270 A1 | 9/2010 | Bogart et al. |
| 2011/0040308 A1 | 2/2011 | Cabrera et al. |

\* cited by examiner

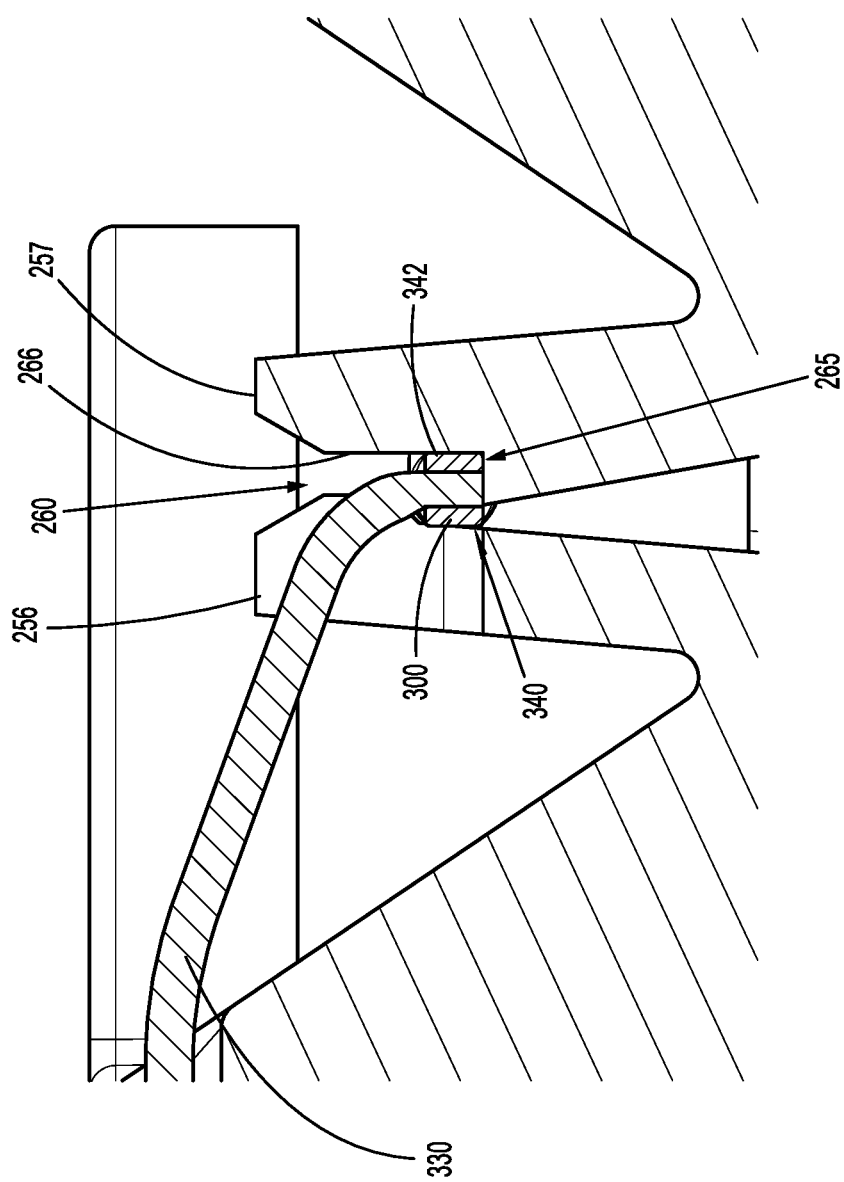

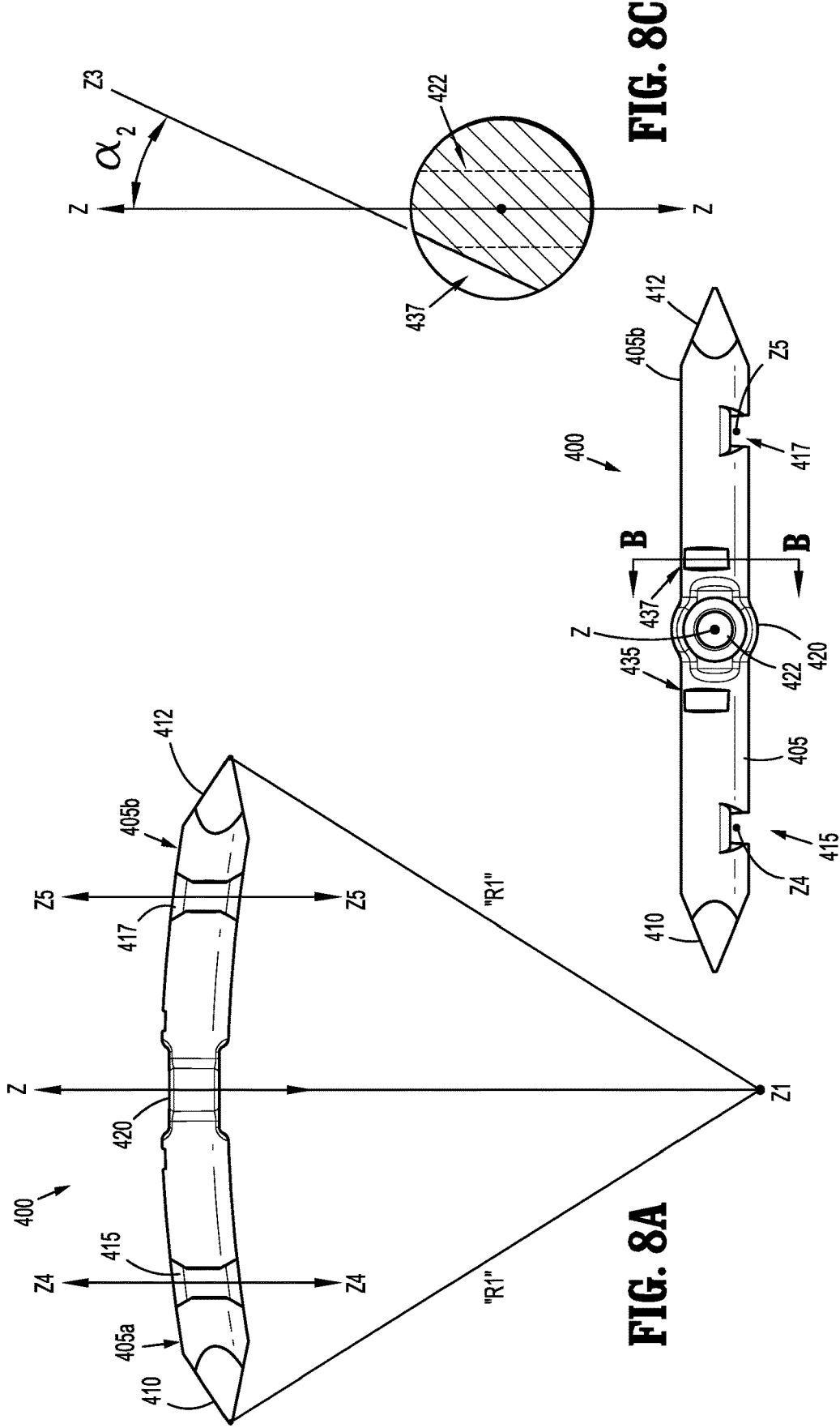

US 10,973,510 B2

NEEDLE LOADING UNIT FOR SURGICAL SUTURING APPARATUS

CROSS-REFERENCE TO RELATED APPLICATIONS

This application claims the benefit of and priority to U.S. Provisional Patent Application No. 62/500,019 filed May 2, 2017, the entire disclosure of which is incorporated by reference herein.

BACKGROUND

1. Technical Field

The present disclosure generally relates to a surgical suturing apparatus, and more particularly, to needle loading units for use with a surgical suturing apparatus.

2. Background of Related Art

Advances in recent years to reduce the invasiveness of surgical procedures include laparoscopic and endoscopic surgery. Generally, such procedures involve making a small incision through body walls to provide access to a target site. Trocar tubes or cannula devices are advanced through the incision and left in place in the body wall to provide access for surgical tools. The surgeon can then perform diagnostic and therapeutic procedures at the surgical site using the surgical tools.

In many surgical procedures, including those involved in endoscopic or laparoscopic surgery, it is often necessary to suture bodily organs or tissue. In such surgical procedures, it is necessary to manipulate a surgical needle, having a length of suture material attached thereto, with, e.g., a surgical suturing apparatus. A need exists for simple and effective loading units for precisely positioning a surgical needle in a surgical suturing apparatus.

SUMMARY

The present disclosure relates to a loading unit assembly for use with a surgical suturing apparatus.

According to an aspect of the present disclosure, the loading unit assembly may include a support structure including a first finger and a second finger adjacent to the first finger. The first and second fingers may define a first channel therebetween. The support structure may also include a third finger defining a seat portion and a back portion. The seat and back portions may be in facing relation with the first and second fingers. The third finger and the first and second fingers may define a second channel therebetween. The support structure may be configured to releasably secure a surgical needle loaded in the second channel and in abutment with at least the seat portion.

In embodiments, the loading unit further includes a surgical needle having a central crimped portion defining an aperture therethrough. A length of suture material may also be provided and may have a first end portion and a second end portion. The first end portion of the length of suture material may be secured to the aperture of the central crimped portion of the surgical needle and the second end portion of the length of suture material may be releasably secured to a base of the loading unit.

Each of the first and second fingers may include a tooth on an outer surface thereof. The surgical needle may further define a first groove and a second groove on an outer surface thereof. The teeth of the first and second fingers may be respectively selectively receivable in the first and second grooves of the surgical needle. The central crimped portion of the surgical needle may be disposed on the seat portion of the third finger such that a longitudinal axis of the surgical needle may be oriented orthogonally relative to a longitudinal axis of the support structure.

In embodiments, a central longitudinal axis of the first and second grooves may be oriented at an angle relative to a central axis of the aperture of the central crimped portion. The angle may be from about 5 degrees to about 40 degrees.

When the teeth of the first and second fingers are selectively received in the respective first and second grooves of the surgical needle, the first end portion of the length of the suture material may extend perpendicularly relative to the seat portion of the third finger, and the first end portion of the length of suture material may extend between the first channel defined between the first and second fingers. When the teeth of the first and second fingers are selectively received in the respective first and second grooves of the surgical needle, the first end portion of the length of the suture material may extend parallel relative to the seat portion of the third finger, and the first end portion of the length of suture material may extend between the first channel defined between the first and second fingers.

In embodiments, the surgical needle may further define a pair of recesses on the outer surface thereof. A central longitudinal axis of each of the first and second recesses may be perpendicular to the central axis of the aperture of the central crimped portion or parallel to the central axis of the aperture of the central crimped portion.

According to another aspect of the present disclosure, a loading unit for use with a surgical suturing apparatus is provided, the loading unit including a body portion and a support structure disposed on the body portion and configured for releasably securing a surgical needle. The support structure may include a first finger and a second finger adjacent to the first finger. The first and second fingers may define a first channel therebetween. The support structure may include a third finger defining a seat portion and a back portion. The seat and back portions of the third finger may be in facing relation with the first and second fingers. The third finger and the first and second fingers may define a second channel therebetween.

In embodiments, each of the first and second fingers may include a tooth on a surface thereof, each tooth of the first and second fingers being in facing relation with the seat portion and the back portion of the third finger.

The loading unit may include an alignment recess formed in the body portion thereof and a plurality of tabs extending from the body portion and adjacent to the alignment recess, the alignment recess and the plurality of tabs configured to slidably receive an elongate shaft assembly of a surgical suturing apparatus.

In embodiments, a central stopping member may be disposed on the body portion between the support structure and the alignment recess, the central stopping member configured to limit advancement of the elongate shaft assembly and a pair of jaw members of the surgical suturing apparatus.

According to another aspect of the present disclosure, a surgical needle is provided, including a cylindrical body having first and second pointed ends and a central crimped portion defining an aperture therethrough, the aperture defining a central axis. A pair of grooves may be defined in the cylindrical body configured to operatively engage with a needle loading unit, the pair of grooves each defining a central longitudinal axis, the central longitudinal axes of the pair grooves being at an angle relative to the central axis of the aperture.

In embodiments, the angle may be from about 5 degrees to about 40 degrees.

A pair of recesses may be defined in the cylindrical body, each recess being configured to releasably engage with needle receiving blades of a pair of jaw members of a surgical suturing apparatus, each recess of the pair of recesses defining a central longitudinal axis. The central longitudinal axis of each recess of the pair of recesses may be parallel or perpendicular to the central axis of the aperture.

In embodiments, a length of suture material may be provided, having a first end portion and a second end portion, the first end portion of the length of suture material secured to the aperture of the central crimped portion of the surgical needle.

The cylindrical body of the surgical needle may define a radius of curvature and an axis defined at the center of the radius of curvature. The axis defined at the center of the radius of curvature may be parallel or perpendicular to the central axis of the aperture.

BRIEF DESCRIPTION OF THE DRAWINGS

FIG. 6 is a side, cross-sectional view of the indicated area of FIG. 4;

FIG. 8A is a side view of a needle in accordance with another embodiment of the present disclosure and configured for use with the loading unit of FIGS. 3A and 3B;

FIG. 8B is a top view of the needle of FIG. 8A;

FIG. 8C is a cross-sectional view of the needle of FIG. 8A taken along the line B-B of FIG. 8B;

DETAILED DESCRIPTION

Figure 1:
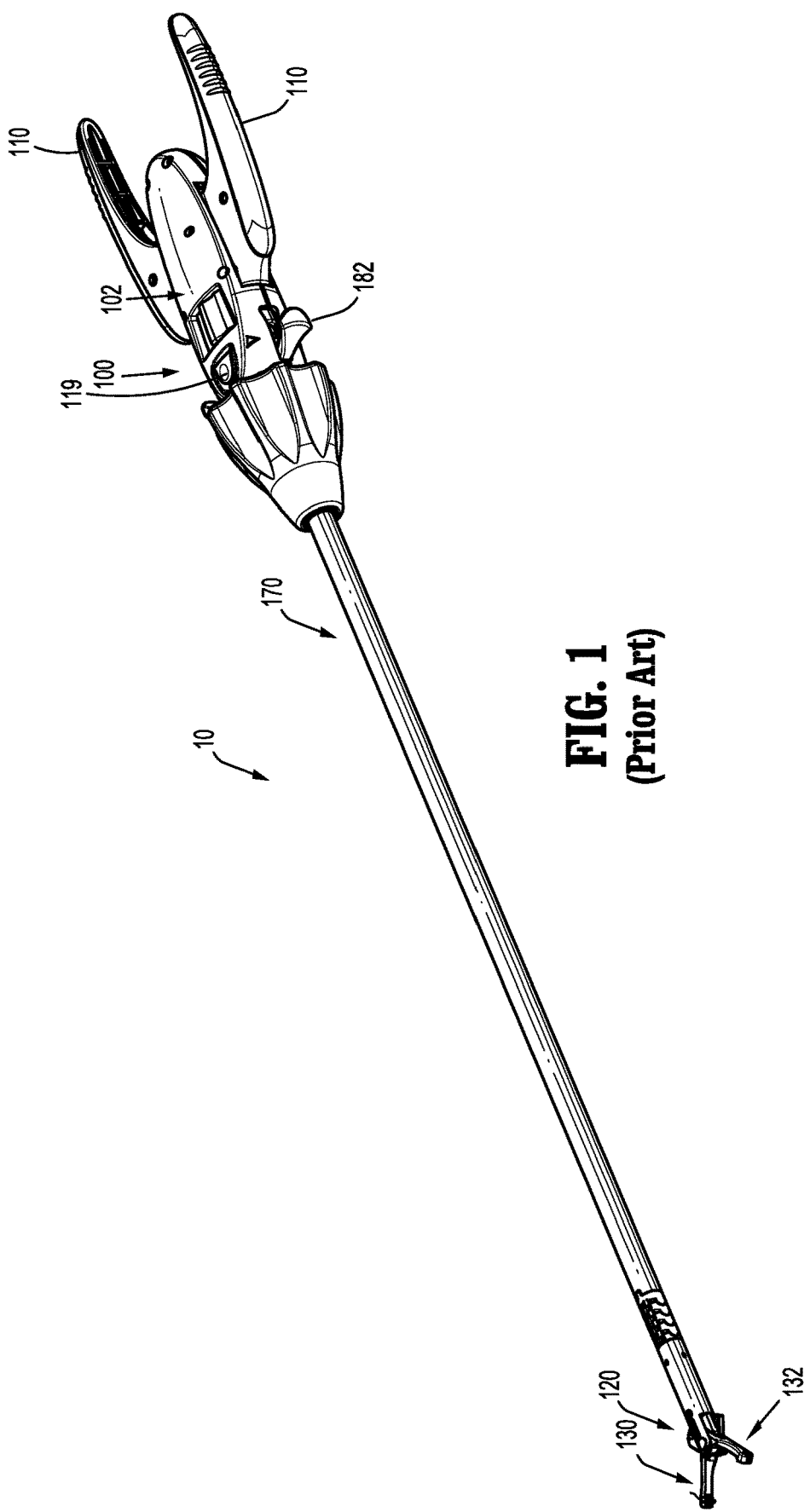
FIG. 1 is a perspective view of a prior art suturing apparatus.

Embodiments of the present disclosure will now be described in detail with reference to the drawings, in which like reference numerals designate identical or corresponding elements in each of the several views. As used herein, the term "clinician" refers to a doctor, nurse, or other care provider and may include support personnel. In the following description, well-known functions or constructions are not described in detail to avoid obscuring the present disclosure in unnecessary detail. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

The present disclosure relates to devices, systems and methods for endoscopic, laparoscopic, endoluminal, and/or transluminal suturing. Specifically, a loading unit is provided for seating of a needle within a pair of jaw members of a surgical suturing apparatus. The loading unit supports a needle and a length of suture material attached thereto to facilitate gripping and loading of the needle and the length of suture material into the pair of jaw members of the surgical suturing apparatus. A support structure of the loading unit stabilizes the needle within the loading unit to ensure adequate transfer of the needle to the jaws of the surgical suturing apparatus during loading.

With reference to FIG. 1, a prior art surgical suturing apparatus is shown and generally identified as reference numeral 10. Suturing apparatus 10 includes a handle assembly 100, an elongate shaft assembly 170 extending distally from handle assembly 100, and a jaw assembly 120 including a pair of jaw members 130, 132 supported on a distal end of elongate shaft assembly 170. Suturing apparatus 10 may be adapted for use in endoscopic or laparoscopic procedures, wherein the elongate shaft assembly 170 is dimensioned for insertion through a tubular cannula structure and into an operative site.

Figure 2:
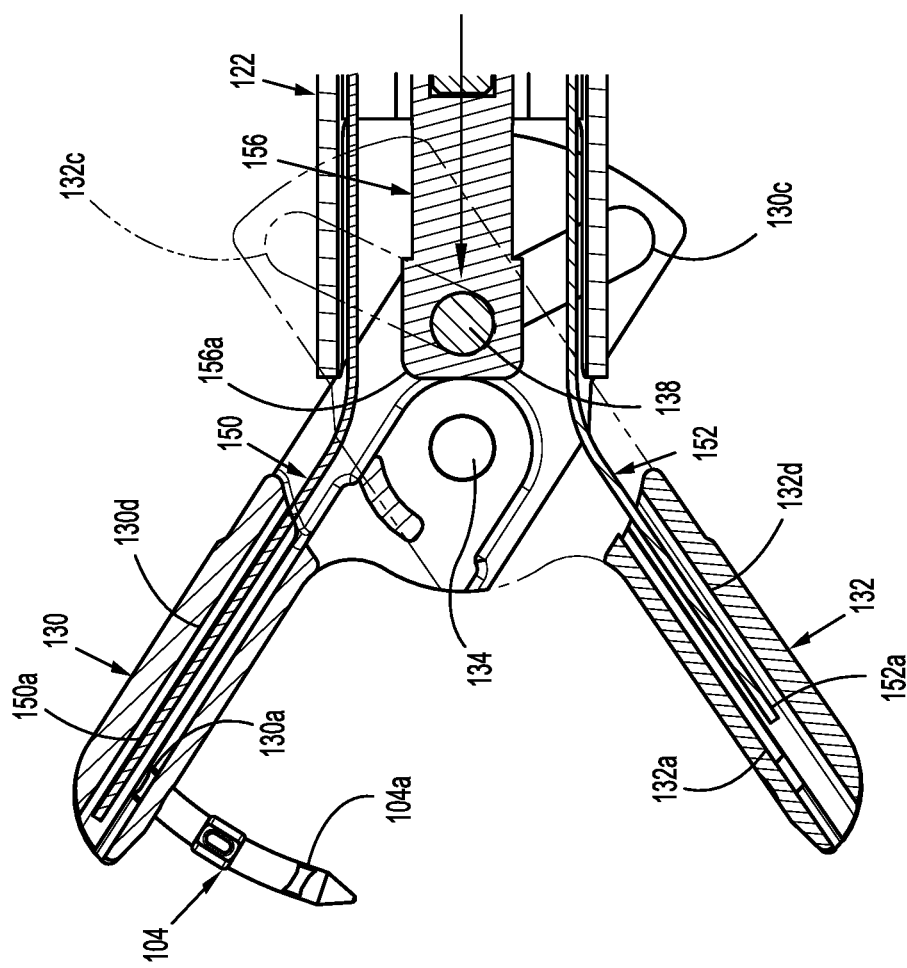
FIG. 2 is partial, cross-sectional view of a prior art jaw assembly of the suturing apparatus of FIG. 1.

With continued reference to FIG. 1 and now with reference to FIG. 2, the handle assembly 100 of the suturing apparatus 10 includes a pair of handles 110 pivotably secured to a housing 102. The handles 110 of suturing apparatus 10 are operatively coupled to an axial rod 156. The axial rod 156 is slidably disposed within the elongate shaft assembly 170 of the suturing apparatus 10. A distal end 156a of the axial rod 156 includes a camming pin 138 mounted thereon. The camming pin 138 of the axial rod 156 rides in angled camming slots 130c, 132c defined in the respective pair of jaws members 130, 132. The pair of jaw members 130, 132 are pivotably mounted on a distal end portion 122 of the elongate shaft assembly 170 of the suturing apparatus 10 via a jaw pivot pin 134. Upon actuating or squeezing the handles 110 of the suturing apparatus 10, the axial rod 156 moves proximally in the longitudinal direction and the camming pin 138 slides within the respective camming slots 130c, 132c of the pair of jaw members 130, 132, which causes the pair of jaw members 130, 132 to transition between an unapproximated position and an approximated position.

The handle assembly 100 further includes a lever 182 pivotably supported in the housing 102 and extending transversely from the housing 102. The lever 182 is operatively coupled to a pair of blades 150, 152 of the pair of jaw members 130, 132. Lever 182 may be pivoted to cause reciprocating axial displacement of the blades 150, 152 of the pair of jaw members 130, 132.

Blades 150, 152 of the pair of jaw members 130, 132 are slidably supported within the elongate shaft assembly 170. Each blade 150, 152 of the pair of jaw members 130, 132 includes a distal end 150a, 152a slidably extending into blade receiving channels 130d, 132d of the pair of jaw members 130, 132, respectively. Recesses 130a, 132a define an opening in the blade receiving channels 130d, 132d of the pair of jaw members 130, 132, respectively, for receiving a needle 104 therein.

The handle assembly 110 further includes a slider 119 operatively coupled with lever 182 to slide the lever 182 distally, which transitions the handle assembly 100 to a reload mode. In the reload mode, both blades 150, 152 of the pair of jaw members 130, 132 are in a distal-most position. In use, the slider 119 of handle assembly 110 of suturing apparatus 10 is actuated (e.g., depressed and/or pushed forward) to the reload mode, causing both blades 150, 152 of the pair of jaw members 130, 132 to be in their distal most position within respective channels 130d, 132d of the pair of jaw members 130, 132 such that respective notches (not shown) of blades 150, 152 of the pair of jaw members 130, 132 are aligned with or in registration with respective recesses 130a, 132a of the pair of jaw members 130, 132. Needle 104 may then be positioned or loaded into a selected one, or both of needle recesses 130a, 132a of the respective pair of jaw members 130, 132 of the suturing apparatus 10 such that as the blades 150, 152 of the pair of jaw members 130, 132 are advanced or retracted, the blades 150, 152 of the pair of jaw members 130, 132 engage or "lock in" a groove 104a formed in the needle 104 when at least a portion of the needle 104 is received within the respective needle recesses 130a, 132a of the pair of jaw members 130, 132.

The lever 182 is then actuated such that only one of the blades 150, 152 of the pair of jaw members 130, 132 is moved into engagement with a groove 104a of the needle 104, and the other blade 150, 152 of the pair of jaw members 130, 132 is disengaged from needle 104. Thus, the needle 104 can be alternated between each jaw of the pair of jaw members 130, 132, as desired. For a detailed discussion of the construction and operation of a surgical suturing apparatus, reference may be made to U.S. Pat. No. 8,628,545, entitled "Endoscopic Stitching Devices," the entire content of which is incorporated herein by reference.

Figure 3A:
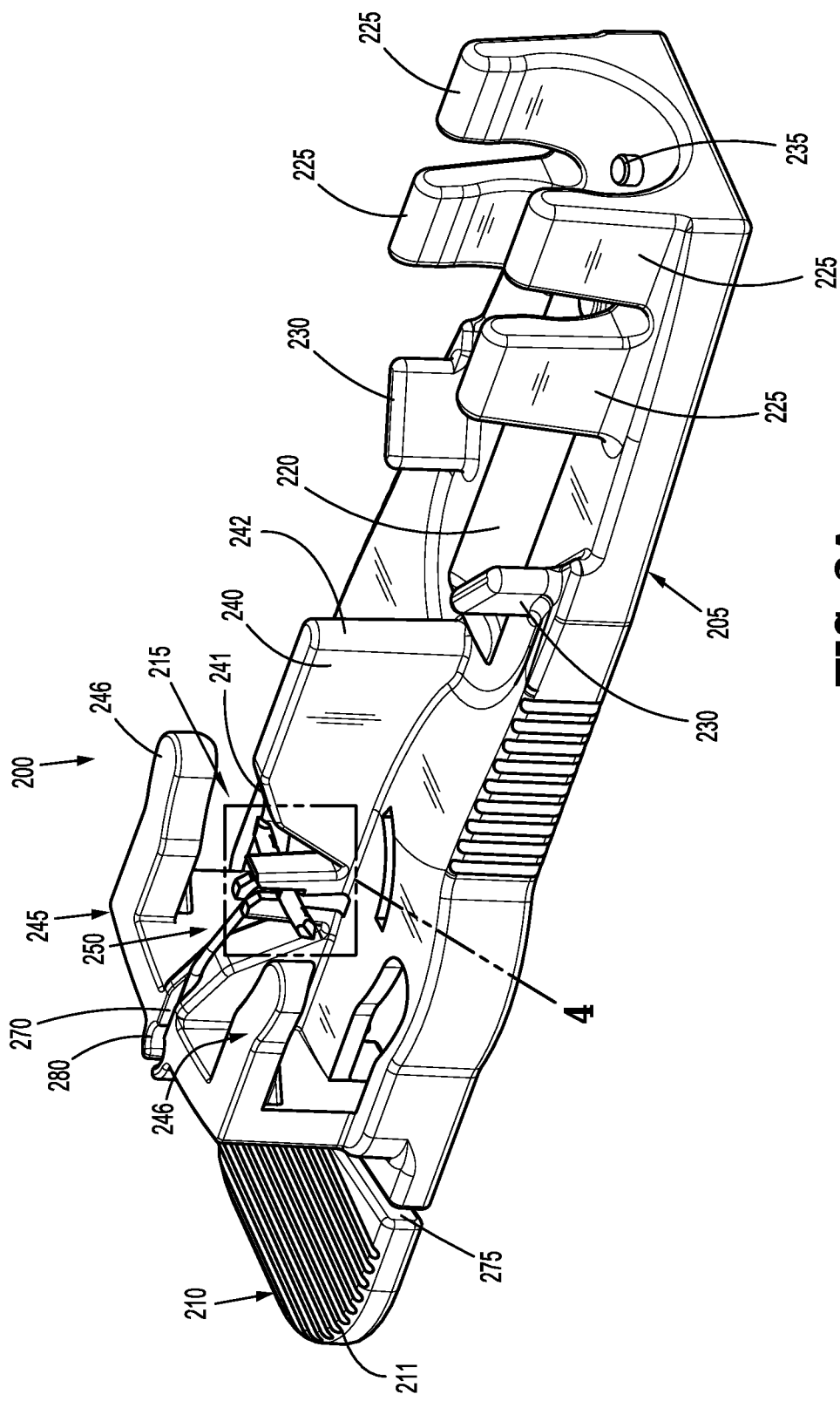
FIG. 3A is a perspective view of a loading unit, for use with the suturing apparatus of FIG. 1, in accordance with an embodiment of the present disclosure.
Figure 3B:
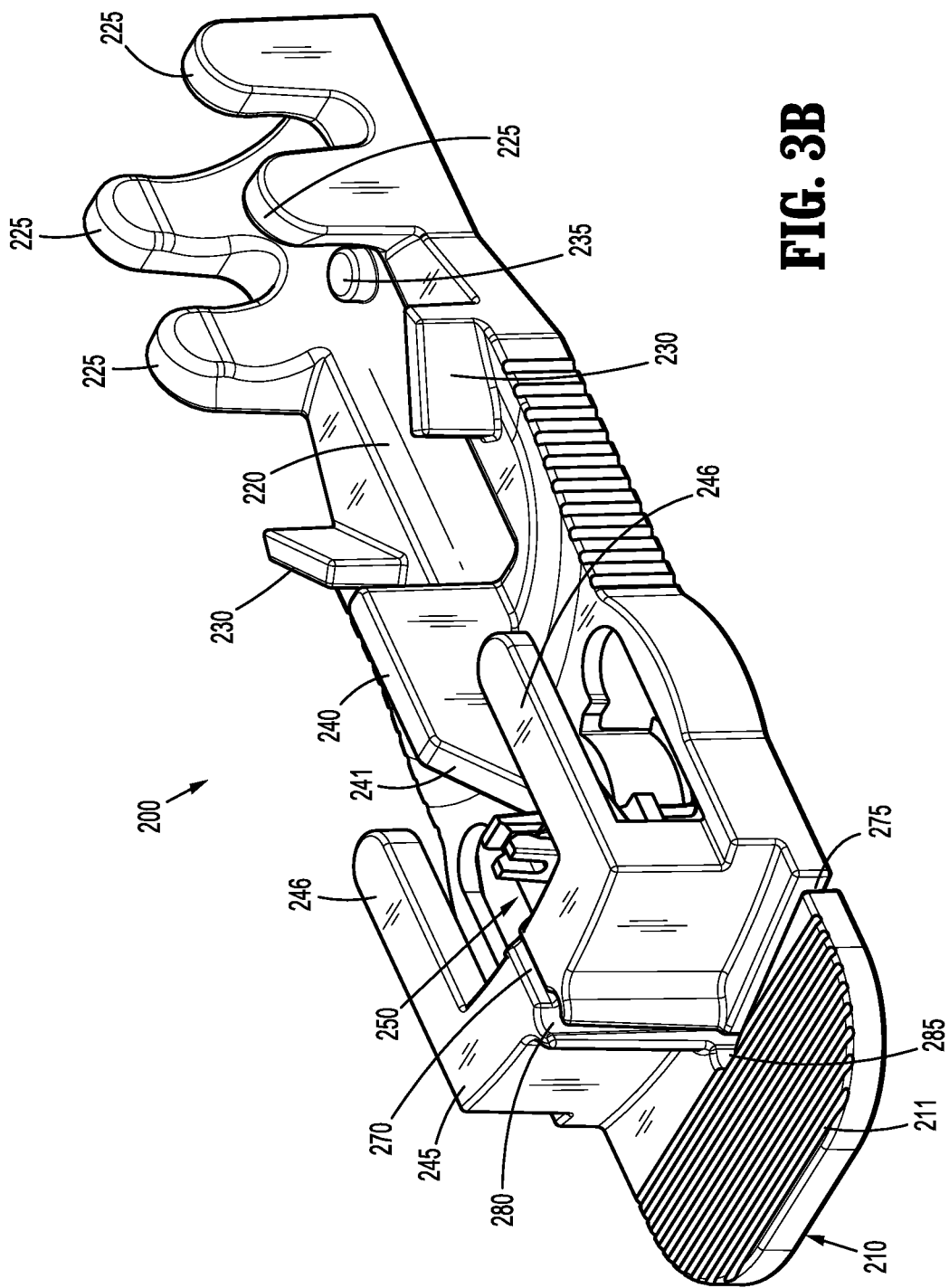
FIG. 3B is a rear, perspective view of the loading unit of FIG. 3A.
Figure 4:
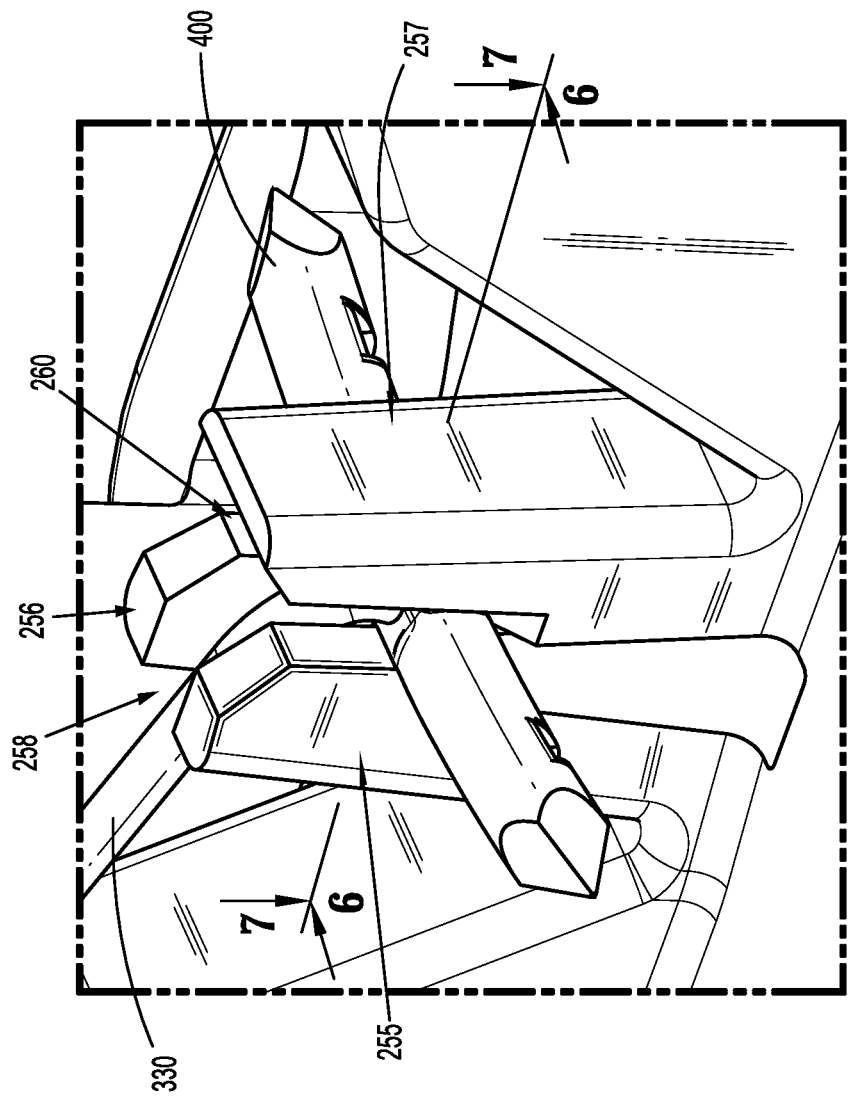
FIG. 4 is a detail view of the indicated area of detail delineated in FIG. 3A.

With reference to FIGS. 3A and 3B, a loading unit for use with the suturing apparatus 10 is provided in accordance with the present disclosure and generally designated as 200. Loading unit 200 is used to secure a needle 300 (FIGS. 5A and 5B) within the pair of jaw members 130, 132 of the suturing apparatus 10. The loading unit 200 generally includes a body portion 205 having a handle or a finger tab 210 extending proximally therefrom. The finger tab 210 of the loading unit 200 may include a plurality of ridges 211, or be otherwise textured, to enhance the gripping ability of the user.

A needle support structure 215 of loading unit 200 is formed on the body portion 205 of the loading unit 200 to mount, support and/or suspend the needle 300, as will be described below. The loading unit 200 is further provided with various apparatus receiving structures for guiding the pair of jaw members 130, 132 of the suturing apparatus 10 adjacent to the support structure 215 of the loading unit 200 for grasping of the needle 300 within the needle recesses 130a, 132a of the respective pair of jaw members 130, 132 for removal therewith.

In particular, as seen in FIGS. 3A and 3B, an alignment recess 220 is provided in body portion 205 for guiding the elongate body portion 170 into position on the loading unit 200. The alignment recess 220 includes a plurality of tabs 225 extending therefrom, which surround or flank the elongate body portion 170 of suturing apparatus 10 to ensure proper alignment therewith. A pair of stops 230 are disposed on each side of the alignment recess 220 to ensure proper placement of the pair of jaw members 130, 132 onto the loading unit 200.

Alignment recess 220 further includes a support stud 235 projecting from body portion 205. Support stud 235 may engage with a corresponding recess (not shown) in a distal portion of the elongate body portion 170 to maintain the suturing apparatus 10 and/or loading unit 200 in proper alignment.

A central stopping member 240 is disposed on the body portion 205 of the loading unit 200 between the support structure 215 and the alignment recess 220. The central stopping member 240 of the loading unit 200 includes a ramped surface 241 formed on a leading portion thereof. When the elongate body portion 170 of the suturing apparatus 10 is inserted into the alignment recess 220 of the loading unit 200, the distal end of the elongate body portion 170 of the suturing apparatus 10 will abut a trailing edge 242 of the central stopping member 240 of the loading unit 200 to thereby limit advancement of the pair of jaw members 130, 132 of the suturing apparatus 10 within the loading unit 200.

The loading unit 200 further includes various structure or safety features to ensure that the needle 300 is not removed from the loading unit 200 until the needle 300 has been firmly grasped, e.g., by completely closing the pair of jaw members 130, 132 of the suturing apparatus 10. In particular, the loading unit 200 includes a safety feature 245 to prevent lifting of the pair of jaw members 130, 132 of the suturing apparatus 10 away from body portion 205, and thus lifting of the needle 300 out of the loading unit 200 before the needle 300 has been firmly grasped by the pair of jaw members 130, 132 of the suturing apparatus 10.

Safety feature 245 includes a pair of blocking members 246 which are suspended above and adjacent either side of central stopping member 240. Blocking members 246 prevent vertical movement of the pair of jaw members 130, 132 of the suturing apparatus 10 out of body portion 205 of the loading unit 200 until the pair of jaw members 130, 132 of the suturing apparatus 10 are closed. The ramped surface 241 of the central stopping member 240 of the loading unit 200 helps prevent premature longitudinal withdrawal of the pair of jaw members 130, 132 of the suturing apparatus 10 from the loading unit 200.

Once the pair of jaw members 130, 132 of the suturing apparatus 10 have been firmly and positively closed about the needle 300 and the blades 150, 152 thereof engaging needle 300, the closed pair of jaw members 130, 132 may be lifted vertically through a gap 250 formed between blocking members 246 of safety feature 245 of the loading unit 200 in order to remove the needle 300 from the loading unit 200. Thus, the blocking members 246 of the safety feature 245 of the loading unit 200, in conjunction with the ramped surface 241 of the central stopping member 240 of the loading unit 200, aid in ensuring that the needle 300 is not removed from the loading unit 200 until the pair of the jaw members 130, 132 of the suturing apparatus 10 have been fully closed and have firmly grasped the needle 300.

Referring now to FIGS. 4 to 7, the support structure 215 of the loading unit 200 is used to maintain the needle 300 in a secure and stabilized position to ensure accurate loading of the needle 300 into the pair of jaw members 130, 132 of the suturing apparatus 10. The support structure 215 of the loading unit 200 includes a first finger 255 and a second finger 256 disposed adjacent to and/or in parallel relation with, the first finger 255. The first finger 255 and the second finger 256 define a first channel 258 therebetween. The first finger 255 includes a tooth 255*a* (FIG. 7) on a trailing surface thereof. Likewise, the second finger 256 includes a tooth 256*a* (FIG. 7) defined on a trailing surface thereof. A third finger 257 trails or is adjacent to the first and second fingers 255, 256 and is in facing relation therewith. A second channel 260 is defined between the first and second fingers 255, 256, and the third finger 257. As shown in at least FIG. 6, the third finger 257 has a substantially seat shaped profile. Specifically, the third finger 257 includes a seat, shoulder, or ledge portion 265 and a back portion 266 extending therefrom. The first, second, and third fingers 255, 256, 257 of the support structure 215 of the loading unit 200 cooperate to hold the needle 300 such that a longitudinal axis of the needle 300 is oriented orthogonally relative to the support structure 215 of the loading unit 200.

Figures 5A, 5B, 5C:
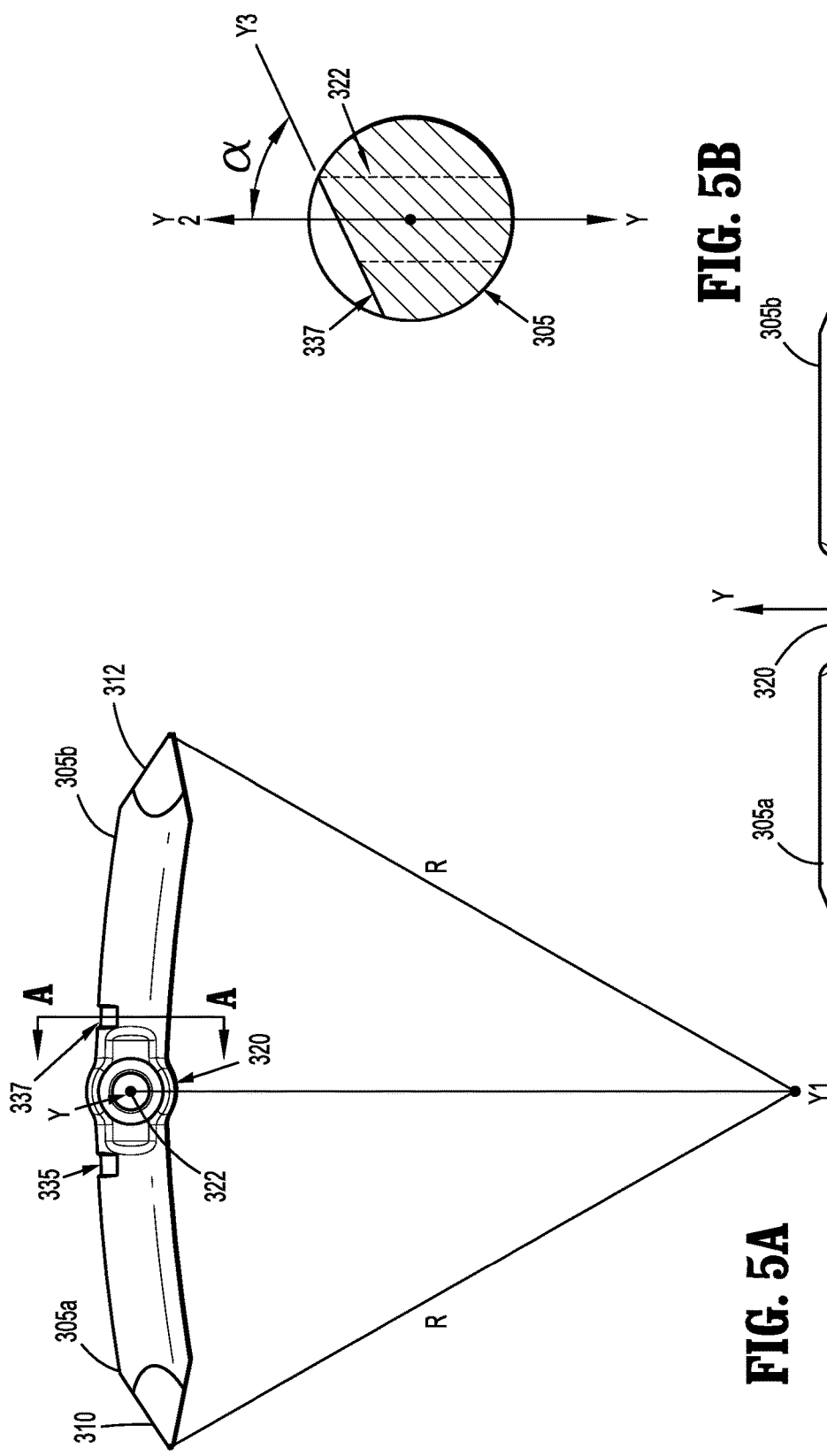
FIG. 5A is a top view of a needle configured for use with the loading unit of FIGS. 3A and 3B.
FIG. 5B is a cross-sectional view of the needle of FIG. 5A taken along the line A-A of FIG. 5A.
FIG. 5C is a side view of the needle of FIG. 5A.

With reference to FIGS. 5A, 5B, and 5C, the needle 300 is configured for use with the loading unit 200. Specifically, the needle 300 is configured to be releasably retained between the first, second, and third fingers 255, 256, 257 of the support structure 215 of the loading unit 200 (FIGS. 3A, 3B, 4, 6, 7). The needle 300 has a generally cylindrical body 305 with first and second sharp ends 310, 312 extending from respective ends 305*a*, 305*b* of the cylindrical body 305. The cylindrical body 305 of the needle 300 is shown as having a generally curved or arcuate configuration, but it is also contemplated that the needle 300 may have any suitable configuration or shape for penetrating and/or suturing tissue therewith. Needle 300 defines a radius of curvature "R." A pair of recesses 315, 317 are formed in the cylindrical body 305 of the needle 300 for engagement with respective blades 150, 152 of the pair of jaw members 130, 132 of the suturing apparatus 10 to secure the needle in the pair of jaw members 130, 132 of the suturing apparatus 10 therewith (FIGS. 2, 5C).

A central crimped or flattened portion 320 of the needle 300 defines an aperture 322 therein and is formed transversely therethrough. Aperture 322 is configured for securing a length of suture material 330 (FIGS. 3A, 3B, 4, 6, 7) therewith. A first groove 335 and a second groove 337 are formed in the cylindrical body 305 of the needle 300 adjacent to opposed sides of the crimped portion 320 of the needle 300. The aperture 322 of the needle 300 defines a central axis "Y" (FIG. 5A). An axis "Y1" is defined at the center of the radius of curvature "R," and as shown in the top view of the needle 300 in FIG. 5A. The central axis "Y" of aperture 322 is parallel to axis "Y1" and spaced a distance therefrom.

As shown in FIGS. 5A and 5B, first and second grooves 335, 337 may be formed in cylindrical body 305 of the needle 300. The first and second grooves 335, 337 define a central longitudinal axis "Y2" (not explicitly shown) and "Y3," respectively. Central longitudinal axes "Y2" and "Y3" of the first and second grooves 335, 337, respectively, are oriented at an angle "a" relative to the central axis "Y" of the aperture 322 of the needle 300. In embodiments, the angle "a" may be from about 5 degrees to about 40 degrees.

With reference to FIG. 5C, the pair of recesses 315, 317 define central longitudinal axes "Y4" and "Y5," respectively. The central longitudinal axes "Y4" and "Y5" of the recesses 315, 317 of the needle 300 may be oriented perpendicular to the central axis "Y" of the aperture 322 of the needle 300 and the axis "Y1" of the radius of curvature "R" of the needle 300.

The first and second grooves 335, 337 of the needle 300 are configured to engage the teeth 255*a*, 256*a* of the first and second fingers 255, 256 of the support structure 215 of the loading unit 200 to secure the needle 300 in position within the support structure 215 of the loading unit 200. The crimped portion 320, the recesses 315, 317, and the first and second grooves 335, 337 of needle 300 may be formed by any known process, such as crimping, tube drawing, molding, or the like.

Needle 300 is provided with the suture material 330 (FIGS. 3A, 3B, 4, 6 and 7) as a needle assembly. Suture material 330 is secured to the aperture 322 of the crimped portion 320 of the needle 300. In order to secure the suture material 330 within the loading unit 200, until such time as the needle 300 is removed from the loading unit 200, the loading unit 200 includes a guide notch 270 (FIGS. 3A and 3B), which guides the suture material 330 into a hollow body cavity (not shown) of loading unit 200. A slot 275 aids in ease of manufacture of the loading unit 200 by allowing easier insertion of the suture material 330 into the loading unit 200.

With the needle 300 loaded into the support structure 215, the suture material 330 of the needle 300 extends through the first channel 258 defined between the first and second fingers 255, 256 of the support structure 215, and through a conduit or channel 280 into an aperture 285 formed in a trailing portion of the finger tab 210 of the loading unit 200. The suture material 330 of needle 300 then extends into, and is secured within, the hollow body cavity (not shown) defined in the base of the loading unit 200. Thus, the suture material 330 of needle 300 may be neatly and securely stored within the loading unit 200 prior to removal of the needle 300 from the loading unit 200.

Figure 7:
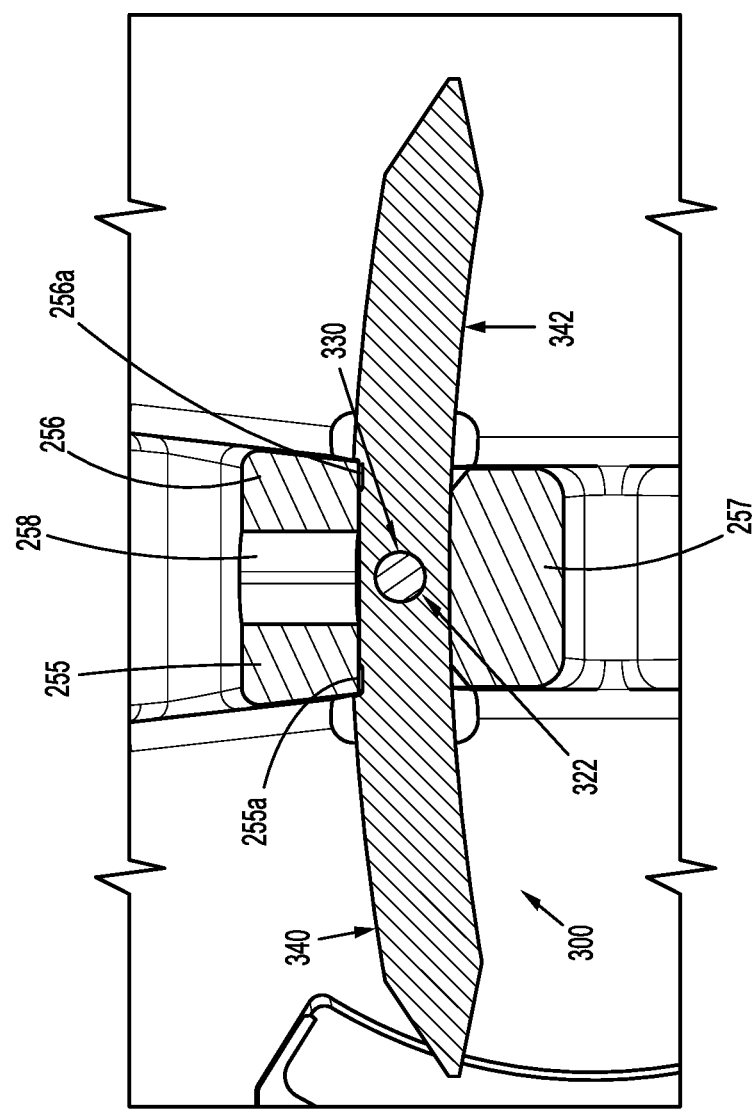
FIG. 7 is a top, cross-sectional view of the indicated area of FIG. 4.
Figure 9A:
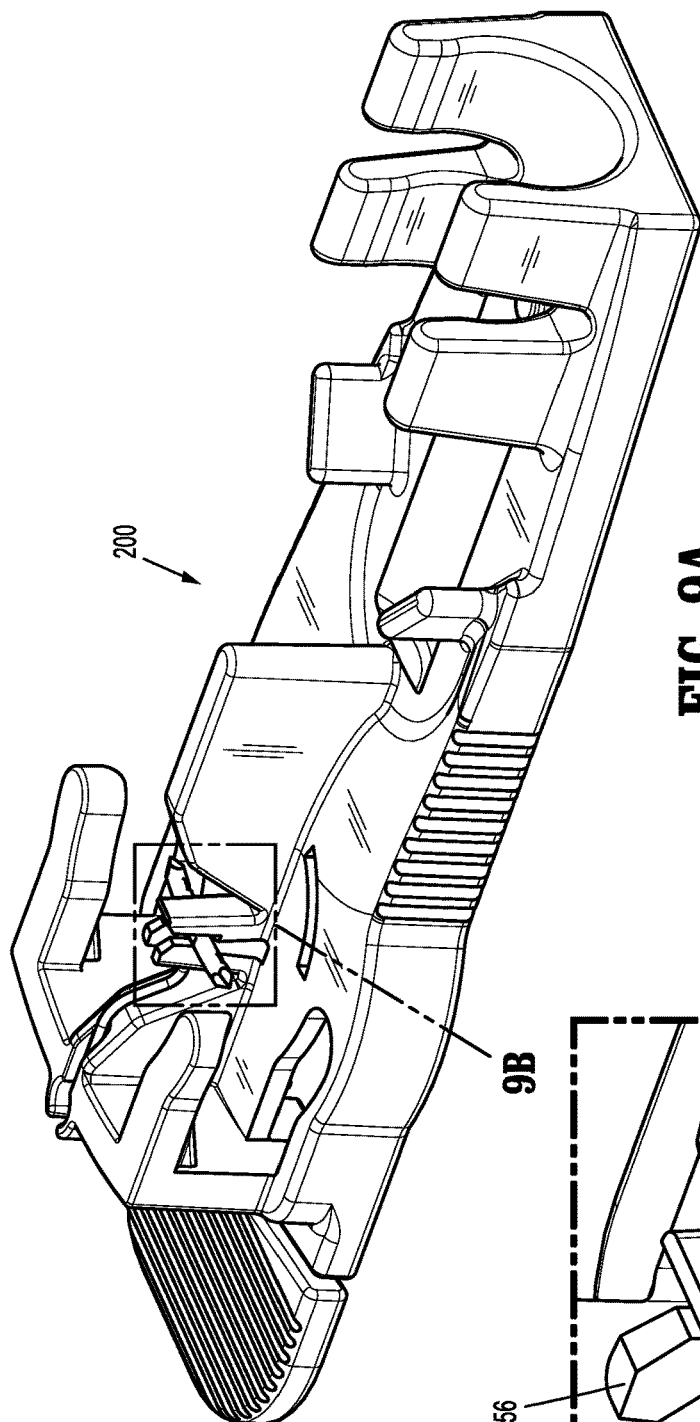
FIG. 9A is a perspective view of the loading unit of FIGS. 3A and 3B with the needle of FIG. 8A disposed therein.
Figure 9B:
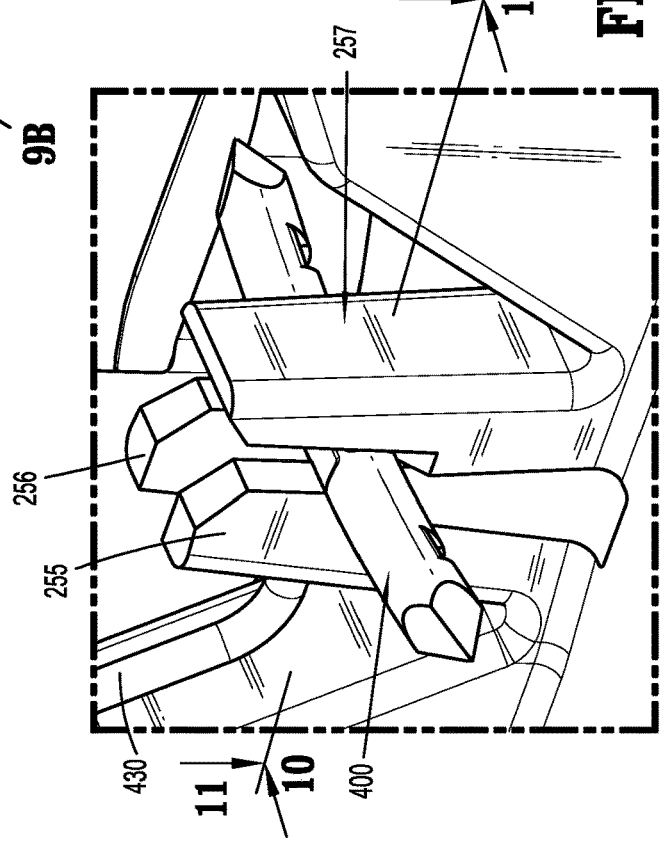
FIG. 9B is a detail view of the indicated area of detail delineated in FIG. 9A.

As shown in FIGS. 6 and 7, needle 300 is shown disposed on the support structure 215 of the loading unit 200. Specifically, needle 300 is oriented such that the crimped portion 320 of needle 300 is in facing relationship with the seat portion 265 of the support structure 215 of the loading unit 200. The suture material 330 of the needle assembly extends transversely from the aperture 322 of the crimped portion 320 of the needle 300 and out through the first channel 258 defined between the first and second fingers 255, 256 of the support structure 215, as described above. The first and second grooves 335, 337 of the needle 300 are engaged with the teeth 255*a*, 256*a* of the first and second fingers 255, 256 of the support structure 215 to stabilize the needle 300 from a first side 340 of the needle. A second side 342 of the needle 300 is supported via the back portion 266 of the support structure 215 of the loading unit 200.

In use, suturing apparatus 10 is first transitioned to the reload mode by actuating slider 119 (FIG. 1) distally such that both blades 150, 152 (FIG. 2) of the pair of jaw members 130, 132 of the suturing apparatus 10 are in the distal-most position. In this manner, respective notches (not shown) of the blades 150, 152 are aligned with or in registration with the respective recesses 130*a*, 132*a* defined in the respective pair of jaw members 130, 132. With notches of the blades 150, 152 aligned with or in registration with the respective recesses 130*a*, 132*a* of the respective pair of jaw members 130, 132, the needle 300 may be loaded into a selected one recess 130*a*, 132*a* of the pair of jaw members 130, 132 of the suturing apparatus 10.

The distal end of the elongate shaft assembly 170 of the suturing apparatus 10 is then guided between the plurality of tabs 225 into the alignment recess 220 of the loading unit 200. The pair of stops 230 disposed on each side of the alignment recess 220 ensure proper placement of the pair of jaw members 130, 132 onto the loading unit 200. The suturing apparatus 10 is advanced until the distal end of the elongate shaft assembly 170 abuts trailing edge 242 of central stopping member 240 to limit advancement of the suturing apparatus 10 and the pair of jaw members 130, 132 therewith. The pair of jaw members 130, 132 are then adjacent to the needle 300 such that the needle 300 is positioned between the pair of jaw members 130, 132. Upon actuation of the handle 110 of the suturing apparatus 10, the pair of jaw members 130, 132 close upon the first and second sharp ends 310, 312 of the needle 300, into recesses 130a, 132a of the pair of jaw members 130, 132, to load the needle 300 between the pair of jaw members 130, 132 of the suturing apparatus 10.

Once needle 300 is loaded or at least partially inserted into recesses 130a, 132a of the pair of jaw members 130, 132, the notches of the blades 150, 152 are in registration with the respective recesses 315, 317 of needle 300. Once the pair of jaw members 130, 132 of the suturing apparatus 10 are firmly closed about the needle 300, the pair of jaw members 130, 132 may be lifted vertically through the gap 250 between the blocking members 246 of the loading unit 200 in order to remove the needle 300 from the support structure 215 of the loading unit 200. The blocking members 246 aid in ensuring that the needle 300 is not removed from the loading unit 200 until the pair of jaw members 130, 132 have been fully closed to firmly grasp the needle 300.

Prior to or after removal of the pair of jaw members 130, 132 from the loading unit 200, and with the handle 110 actuated, and with needle 300 positioned such that the notches of the blades 150, 152 are in registration with the needle recesses 130a, 130b, lever 182 is actuated or rotated so that only one blade 150, 152 of the pair of jaw members 130, 132 is moved into engagement with the needle 300 to hold needle 300, and the other blade 150, 152 of the pair of jaw members 130, 132 is disengaged from the needle 300. With only one blade 150, 152 of the pair of jaw members 130, 132 engaged with the needle 300, following removal of the pair of jaw members 130, 132 from the needle loading unit 200, the handle 110 of the handling assembly 100 of the suturing apparatus 10 may be released, thereby moving the axial rod 156 distally to open the pair of jaw members 130, 132.

With the pair of jaw members 130, 132 of the suturing apparatus 10 in the open position and the needle 300 loaded and held in just one jaw member 130 or 132, the pair of jaw members 130, 132 of the suturing apparatus 10 may be positioned about or over a target tissue and handles 110 may be actuated to approximate the pair of jaw members 130, 132. As the pair of jaw members 130, 132 of the suturing apparatus 10 are approximated, one of the first or second sharp ends 310, 312 of the needle 300 is penetrated through the target tissue and enters the opposed jaw member 130 or 132. With needle 300 in the opposed jaw 130 or 132, the lever 182 is once again actuated or rotated so that the blades 150, 152 of the pair of jaw members 130, 132 are reversed. In so doing, the needle 300 is swapped from one blade 150 or 152 to the other blade 150 or 152, and thus, loaded or held in the other jaw 130 or 132.

With the needle 300 being swapped from one blade 150, 152 to another blade 150, 152, the handles 110 of handle assembly 100 may be released to thereby open the pair of jaw members 130, 132 and draw the needle 300 through the target tissue. In so doing, the suture material 330 of the needle 300 is also drawn through the tissue. The process is repeated, passing the needle 300 between the pair of jaw members 130, 132 and drawing the suture material 330 of the needle 300 through the target tissue, thereby suturing the target tissue as needed or desired.

Turning now to FIGS. 8A, 8B, and 8C an alternative embodiment of a needle is shown and generally designated as 400. The needle 400 has a generally cylindrical body 405 with first and second sharp ends 410, 412 extending from respective ends 405a, 405b of the cylindrical body 405 of the needle 300. A pair of recesses 415, 417 are formed in the cylindrical body 405 of the needle 400 for engagement with the blades 150, 152 of the pair of jaw members 130, 132 of the suturing apparatus 10 to secure the needle in the pair of jaw members 130, 132 of the suturing apparatus 10 therewith. A crimped portion 420 of the needle defines an aperture 422 therein and formed transversely therethrough for securing a length of suture material 430 (FIGS. 9A, 9B, 10, and 11) therewith. A first groove 435 and a second groove 437 are formed in the cylindrical body 405 of the needle 400 adjacent to the crimped portion 420 of the needle 400 and are configured to engage the teeth 255a, 256a of the first and second fingers 255, 256 of the support structure 215 of the loading unit 200 to secure the needle 400 in position within the support structure 215 of the loading unit 200.

The aperture 422 of the needle 400 defines a central axis "Z" (FIGS. 8A-8C). The needle 400 has a substantially arcuate shape defining a radius of curvature "R1." An axis "Z1" is defined at the center of the radius of curvature "R," and as shown in the profile view of the needle 400 in FIG. 8A. The central axis "Z" of the aperture 422 is perpendicular to axis "Z1" and may intersect one another.

As shown in FIGS. 8B and 8C, first and second grooves 435, 437 may be formed in cylindrical body 405 of the needle 400. The first and second grooves 435, 437 of the needle 300 define central longitudinal axes "Z2" (not explicitly shown) and "Z3," respectively. Central longitudinal axes "Z2" and "Z3" of the first and second grooves 435, 437 are oriented at an angle "$\alpha_2$" relative to the central axis "Z" of the aperture 422 of the needle 400. In embodiments, the angle "$\alpha_2$" may be from about 5 degrees to about 40 degrees.

With reference to FIGS. 8A and 8C, the pair of needle recesses 415, 417 may define central longitudinal axes "Z4" and "Z5." Central longitudinal axes "Z4" and "Z5" of the pair of needle recesses 415, 417 may be parallel to the central axis "Z" of the aperture 422 of the needle 400.

Figure 10:
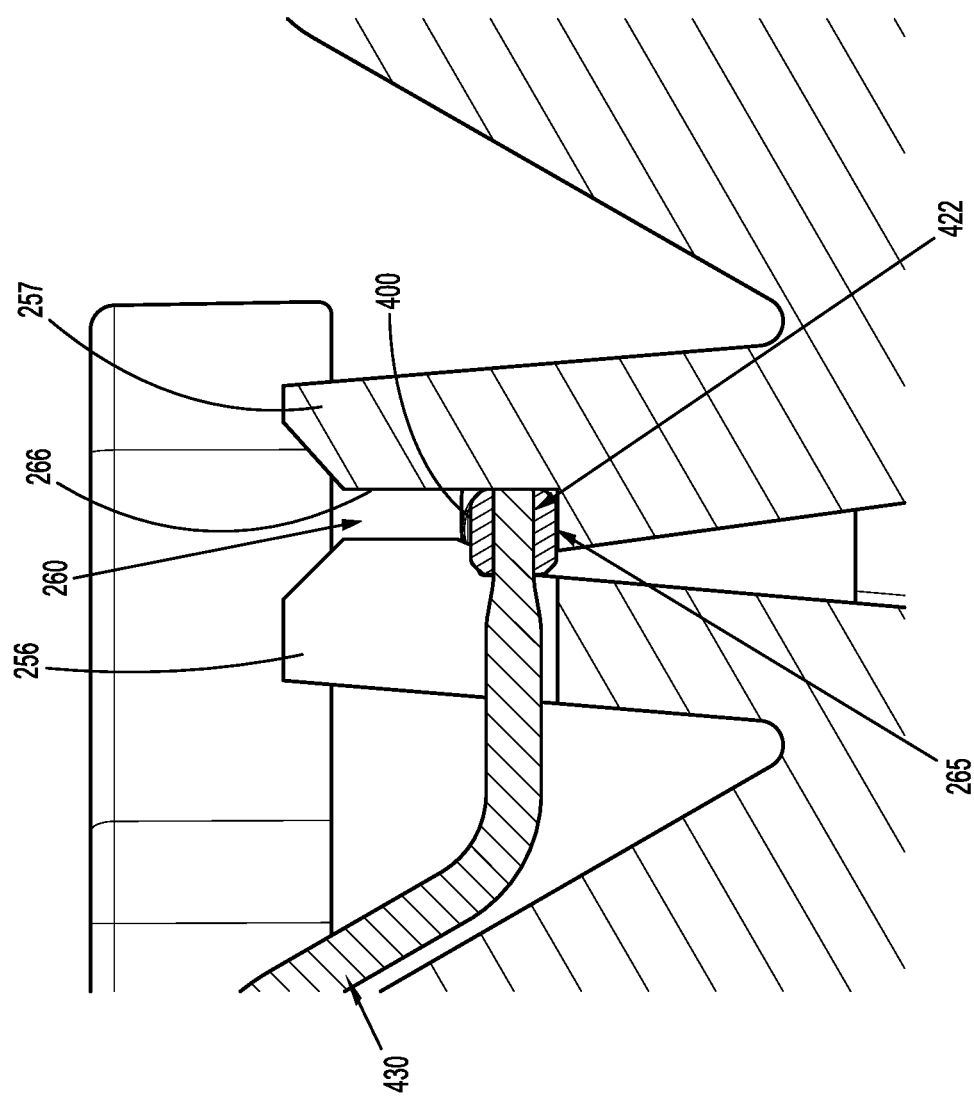
FIG. 10 is side, cross sectional view of the indicated area of detail of FIG. 9B.
Figure 11:
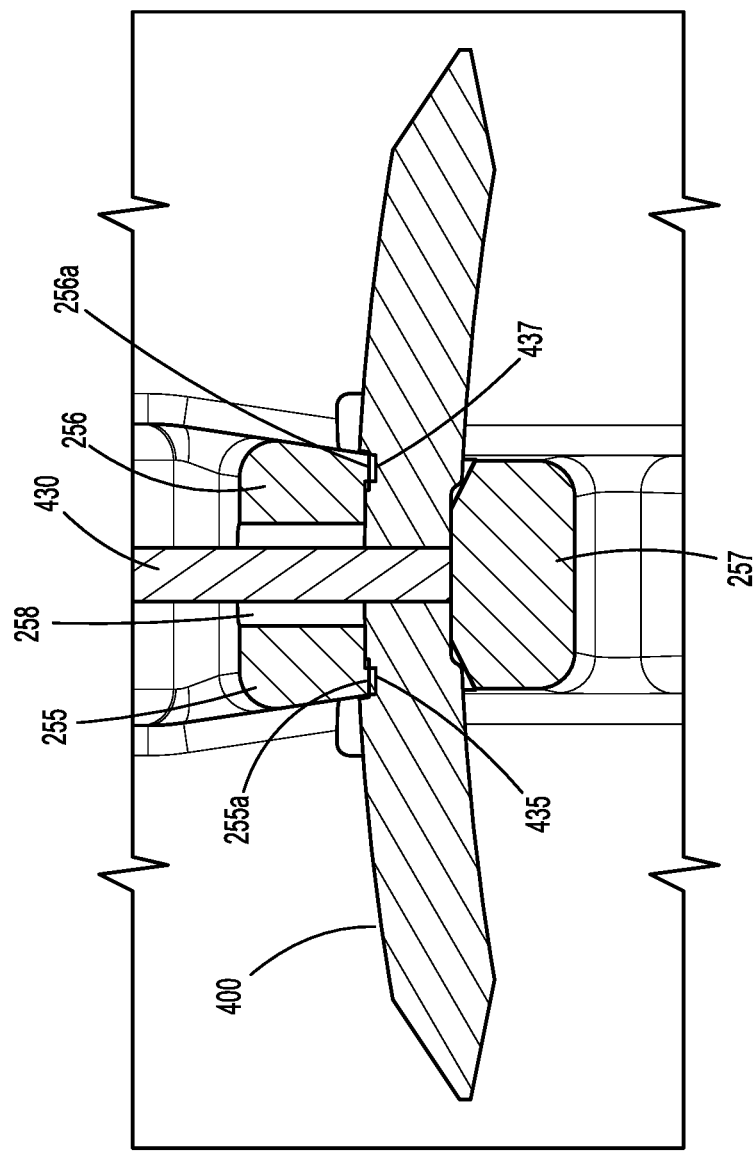
FIG. 11 is a top, cross sectional-view of the indicated area of detail of FIG. 9B.

The first, second, and third fingers 255, 256, 257 of the support structure 215 of the loading unit 200 cooperate to hold the needle 400 such that a longitudinal axis of the needle 400 is oriented orthogonally relative to the support structure 215 of the loading unit 200. The needle 400 is substantially similar to the needle 300 described above except that the crimped portion 420 of the needle 400 is offset, e.g., 90 degrees versus the crimped portion 320 of the needle 300. With the crimped portion 420 of needle 400 offset, needle 400 is orientated in the support structure 215 of the loading unit 200 such that the suture material 430 of needle 400 is parallel with the seat portion 265 of the third finger 257 of the support structure 215 of the loading unit 200. More specifically, with needle 400 disposed in support member 215, the central axis of the aperture 422 of the crimped portion 420 of the needle 400 is oriented parallel with the seat portion 265 of the third finger 257 such that the suture material 430 extends parallel with the seat portion 265 o the third finger 257 out of aperture 422 of the needle 400 through the second channel 260 defined between first and second fingers 255, 256, as shown in FIG. 10.

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances. The embodiments described with reference to the attached drawings are presented only to demonstrate certain examples of the disclosure. Other elements, steps, methods, and techniques that are insubstantially different from those described above and/or in the appended claims are also intended to be within the scope of the disclosure.

What is claimed is:

1. A loading unit assembly for use with a surgical suturing apparatus, the loading unit assembly comprising:
    a surgical needle having a central crimped portion defining an aperture therethrough, the surgical needle defining a first groove and a second groove on an outer surface thereof;
    a length of suture material having a first end portion and a second end portion, the first end portion of the length of suture material secured to the aperture of the central crimped portion of the surgical needle, the second end portion of the length of suture material releasably secured to a base of the loading unit; and
    a support structure including:
        a first finger;
        a second finger adjacent to the first finger, the first and second fingers defining a first channel therebetween, each of the first and second fingers including a tooth on an outer surface thereof; and
        a third finger defining a seat portion and a back portion, the seat and back portions in facing relation with the first and second fingers, wherein the third finger and the first and second fingers define a second channel therebetween, the support structure configured to releasably secure the surgical needle loaded in the second channel and in abutment with at least the seat portion, wherein each tooth of the first and second fingers is selectively receivable in the first or second groove of the surgical needle.

2. The loading unit assembly of claim 1, wherein the central crimped portion of the surgical needle is disposed on the seat portion of the third finger such that a longitudinal axis of the surgical needle is oriented orthogonally relative to a longitudinal axis of the support structure.

3. The loading unit assembly of claim 2, wherein a central longitudinal axis of the first and second grooves is oriented at an angle relative to a central axis of the aperture of the central crimped portion.

4. The loading unit of claim 3, wherein the angle is from about 5 degrees to about 40 degrees.

5. The loading unit assembly of claim 4, wherein when each tooth of the first and second fingers is selectively received in the corresponding first or second groove of the surgical needle, the first end portion of the length of the suture material extends perpendicularly relative to the seat portion of the third finger, and the first end portion of the length of suture material extends between the first channel defined between the first and second fingers.

6. The loading unit of claim 4, wherein when each tooth of the first and second fingers is selectively received in the corresponding first or second groove of the surgical needle, the first end portion of the length of the suture material extends parallel relative to the seat portion of the third finger, and the first end portion of the length of suture material extends between the first channel defined between the first and second fingers.

7. The loading unit assembly of claim 3, wherein the surgical needle further defines first and second recesses on the outer surface thereof.

8. The loading unit assembly of claim 7, wherein a central longitudinal axis of each of the first and second recesses is perpendicular to the central axis of the aperture of the central crimped portion.

9. The loading unit assembly of claim 7, wherein a central longitudinal axis of each of the first and second recesses is parallel to the central axis of the aperture of the central crimped portion.

10. A loading unit for use with a surgical suturing apparatus, the loading unit comprising:
    a body portion defining an alignment recess;
    a plurality of tabs extending from the body portion and adjacent the alignment recess, the alignment recess and the plurality of tabs configured to slidably receive an elongate shaft assembly of a surgical suturing apparatus; and
    a support structure disposed on the body portion and configured for releasably securing a surgical needle, the support structure including:
        a first finger;
        a second finger adjacent to the first finger, the first and second fingers defining a first channel therebetween; and
        a third finger defining a seat portion and a back portion, the seat and back portions of the third finger in facing relation with the first and second fingers, wherein the third finger and the first and second fingers define a second channel therebetween, wherein each of the first and second fingers includes a tooth on a surface thereof, each tooth of the first and second fingers being in facing relation with the seat portion and the back portion of the third finger.

11. The loading unit of claim 10 further comprising a central stopping member disposed on the body portion between the support structure and the alignment recess, the central stopping member configured to limit advancement of the elongate shaft assembly and a pair of jaw members of the surgical suturing apparatus.

12. A loading unit assembly for use with a surgical suturing apparatus comprising:
    a surgical needle defining first and second grooves on an outer surface thereof; and
    a support structure including:
        a first finger;
        a second finger adjacent to the first finger, the first and second fingers defining a first channel therebetween, each of the first and second fingers includes a tooth on an outer surface thereof; and
        a third finger defining a seat portion and a back portion, the seat and back portions in facing relation with the first and second fingers, wherein the third finger and the first and second fingers define a second channel therebetween, the support structure configured to releasably secure the surgical needle loaded in the second channel and in abutment with at least the seat portion, wherein each tooth of the first and second fingers is selectively receivable in the first or second groove of the surgical needle.

13. The loading unit assembly of claim 12, wherein the surgical needle includes a central crimped portion defining an aperture therethrough, the central crimped portion of the surgical needle disposed on the seat portion of the third finger such that a longitudinal axis of the surgical needle is oriented orthogonally relative to a longitudinal axis of the support structure.

14. The loading unit assembly of claim 13, wherein a central longitudinal axis of the first and second grooves is oriented at an angle relative to a central axis of the aperture of the central crimped portion.

15. The loading unit of claim 14, wherein the angle is from about 5 degrees to about 40 degrees.

16. The loading unit assembly of claim 14, wherein the surgical needle further defines first and second recesses on the outer surface thereof.

17. The loading unit assembly of claim 16, wherein a central longitudinal axis of each of the first and second recesses is perpendicular to the central axis of the aperture of the central crimped portion.

\* \* \* \* \*